United States Patent
Burns et al.

(10) Patent No.: US 9,833,402 B2
(45) Date of Patent: Dec. 5, 2017

(54) COMPOSITION

(71) Applicant: Conopco, Inc., Englewood Cliffs, NJ (US)

(72) Inventors: Sian Ruth Burns, Greasby (GB); Lalitesh Chandra, Great Sutton (GB)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 15/112,696

(22) PCT Filed: Jan. 6, 2015

(86) PCT No.: PCT/EP2015/050115
§ 371 (c)(1),
(2) Date: Jul. 20, 2016

(87) PCT Pub. No.: WO2015/110278
PCT Pub. Date: Jul. 30, 2015

(65) Prior Publication Data
US 2016/0331671 A1    Nov. 17, 2016

(30) Foreign Application Priority Data
Jan. 27, 2014   (EP) .................................... 14152727

(51) Int. Cl.
| A61K 8/894 | (2006.01) |
| A61K 8/25 | (2006.01) |
| A61K 8/58 | (2006.01) |
| A61Q 5/06 | (2006.01) |
| A61K 8/891 | (2006.01) |
| A61K 8/895 | (2006.01) |
| A61K 8/04 | (2006.01) |
| A61K 8/31 | (2006.01) |

(52) U.S. Cl.
CPC ............... *A61K 8/894* (2013.01); *A61K 8/04* (2013.01); *A61K 8/25* (2013.01); *A61K 8/31* (2013.01); *A61K 8/585* (2013.01); *A61K 8/891* (2013.01); *A61K 8/895* (2013.01); *A61Q 5/06* (2013.01); *A61K 2800/594* (2013.01); *A61K 2800/5922* (2013.01)

(58) Field of Classification Search
CPC ...... A61K 2800/5922; A61K 2800/594; A61K 8/04; A61K 8/25; A61K 8/31; A61K 8/585; A61K 8/891; A61K 8/894; A61K 8/895; A61Q 5/06
See application file for complete search history.

(56) References Cited

U.S. PATENT DOCUMENTS

| 4,987,169 A | 1/1991 | Kuwata |
| 5,578,641 A | 11/1996 | Jackson |
| 5,654,362 A | 8/1997 | Schulz, Jr. |
| 5,716,627 A | 2/1998 | Granger |
| 5,747,051 A | 5/1998 | Granger |
| 5,759,556 A | 6/1998 | Burger |
| 6,423,322 B1 * | 7/2002 | Fry .................... A61K 8/042 424/401 |
| 8,222,363 B2 | 7/2012 | Lin |
| 2010/0092408 A1 * | 4/2010 | Breyfogle ............... A61K 8/06 424/59 |
| 2012/0058067 A1 * | 3/2012 | van Gogh ............. A61K 8/342 424/70.9 |
| 2012/0134951 A1 * | 5/2012 | Stasko ................ A61K 9/0014 424/78.06 |

FOREIGN PATENT DOCUMENTS

| EP | 0709084 | 5/1996 |
| EP | 0711558 | 5/1996 |
| EP | 0716849 | 6/1996 |
| EP | 1109527 | 8/2002 |
| GB | 2453952 | 4/2009 |
| WO | WO0015179 | 3/2000 |
| WO | WO0108649 | 2/2001 |
| WO | WO2009042535 | 4/2009 |
| WO | WO2009085444 | 7/2009 |
| WO | WO2011056547 | 5/2011 |
| WO | WO2012168102 | 12/2012 |

OTHER PUBLICATIONS

Estee Lauder Fruition, Extra Multi-Action Complex, Cosmetic Research Int., Aug.-Sep. 1996, pp. 1 to 1.
Max Huber Research Labs, La Mer Serum de la Mer the face Serum, Cosmetic Research Int., Jan.-Feb. 1999 pp. 1-1.
Maybelline Products (various), Cosmetic Research Int., Apr. 1994, pp. 1-3.
Sphingolipid, Wikipedia, May 4, 2012, p. 1-1. In J4394USw-NPLRef1, pp. 1 to 1.
Umbelliferin® Product Data Sheet, Sabinsa Corporation, Jan. 23, 2007, p. 1-1.
IPRP in PCTEP2015050115 dated Jan. 27, 2014.
Search Report and Written Opinion in EP14152727 dated Jun. 5, 2014.
Search Report and Written Opinion in PCTEP2015050115 date4d Mar. 11, 2015.
"Ceramide", International Cosmetic Ingredient Dictionary and Handbook, Seventh Edition, Wenninger et al.,1997, vol. 1, pp. 217-219 & 309.

* cited by examiner

*Primary Examiner* — Mark V Stevens
(74) *Attorney, Agent, or Firm* — Karen E. Klumas

(57) ABSTRACT

Hair treatment composition comprising from 40 to 95% wt. of the composition silicone elastomer, 0.01 to 5% silica and from 0 to 2% wt. water.

11 Claims, No Drawings

COMPOSITION

The present invention relates to a hair composition comprising silicone elastomer.

Despite the prior art there remains a need for improved styling compositions. In particular there remains a need for styling compositions with improved consumer experience during application.

Accordingly, there is provided a hair treatment composition comprising from 40 to 95% wt. of the composition silicone elastomer, 0.01 to 5% silica and from 0 to 2% wt. water.

The composition of the invention provides a superior experience for the consumer during use. In particular, the product behaves as a gel in the hands but softens when rubbed between the hands to give a light dry textured layer which is easily spreadable over the hair. This can be applied to dry or damp hair to give a smooth, soft finish with light hold and frizz reduction.

The product of the invention provides an improved consumer experience in that it is more easily worked into the hair. The composition also has a dry feel when being worked whereas aqueous based products of the prior art and tend to feel wet and sticky. Further, silicone based products in the prior art tend to have low levels of silicones with low viscosity (i.e. non-elastomer) and are difficult to work with the hands since they tend to drip through the fingers. This makes them difficult to work with the hands and also makes them difficult to wash off the hands after use. This also makes them clumpy heavy and greasy.

Silicone elastomers are well known in the art. According to (http://www.dowcoming.com/content/publishedlit/Chapter16.pdf)

"Silicone elastomer dispersions are cross-linked gels that can be prepared through a hydrosilylation reaction. The reaction involves low levels of catalyst, usually platinum derivatives, and is generally run into an adequate solvent. SiH containing silicone polymers are reacted with di-vinylic materials to link independent silicone chains. If the reaction is carried out in cyclic PDMS as the solvent, it leads to the formation of a swollen and loosely-reticulated network or a silicone elastomer dispersion." The silicone elastomers of use in the present invention and their methods of manufacture are described in U.S. Pat. Nos. 4,987,169, 8,222,363 and 5,654,362.

The silicone elastomers used in the present invention are dispersions of a loosely reticulated silicone in a solvent.

Examples of the solvent include isodecane, isodecyl neopentanoate, cyclopentasiloxane, dimethicone, isohexane, vinyl dimethicone and hydrogen dimethicone.

Examples of silicones which may be dispersed in a solvent to form an elastomer include:

Dimethicone/Bis-Isobutyl PPG-20 Crosspolymer, Dimethicone Crosspolymer, Dimethicone, vinyl dimethicone, hydrogen dimethione, 2,4,6,8-tetravinyl cyclotetrasiloxane Isododecane (and) Dimethicone/Bis-Isobutyl PPG-20 Crosspolymer commercially available from Dow Corning as Silicone Elastomer EL-8051;

Isodecyl Neopentanoate (and) Dimethicone/Bis-Isobutyl PPG-20 Crosspolymer commercially available from Dow Corning as Silicone Elastomer EL-8052;

Isohexadecane (and) Dimethicone/Bis-Isobutyl PPG 20 Crosspolymer commercially available from Dow Corning as Silicone Elastomer 9040;

Cyclopentasiloxane (and) Dimethicone Crosspolymer commercially available from Dow Corning as Silicone Elastomer 9041;

Dimethicone(and) Dimethicone Crosspolymer commercially available from Dow Corning as Silicone Elastomer 9045; and Dimethicone, vinyl dimethicone, hydrogen dimethione, 2,4,6,8-tetravinyl cyclotetrasiloxane.

The silicone elastomer (dispersed silicone in solvent) is present in the compositions of the invention at from 40 to 95% wt. of the composition, preferably, at from 42 to 85%.

The composition of the invention also comprises silica. Preferably, the silica is fumed silica.

More preferably, the silica is suspended in oil when added to the composition of the invention. The oil facilitates suspension of the silica within the composition. Where the silica is fumed silica it is preferred that the oil is a light mineral oil or fragrance oil. If heavy mineral oil is used the air in the fumed silica becomes trapped in the oil and the result is an overly thickened composition which is unsuitable for use as a cosmetic preparation to be worked into the hair with the hands.

Preferably, the light mineral oil has a density of from 0.7 to 0.85 g/ml. Density of the mineral oil is also known as specific gravity and is measured according to ASTM D 4052 at 15.6 C.

Preferably, the silica is present at from 0.01 to 5% wt of the composition, more preferably from 0.05 to 2% wt.

Preferably, the composition of the invention additionally comprises volatile silicone. Suitable volatile silicones are well known in the art and include DC245 commercially available from Dow Corning.

Preferably, and when present, the volatile silicone is present at from 1 to 30% wt. of the composition and more preferably from 1 to 5% wt.

Preferably, the composition comprises from 0 to 2% wt. water, more preferably from 0 to 1% wt. water and most preferably from 0 to 0.01% wt. water.

Preferably, the composition of the invention includes a styling aid. Preferred styling aids include silicone resins. A particularly preferred silicone resin is known as an MQ resin.

MQ resins are a condensation product between monofunctional silane (M) and tetrafunctinoal silane (Q). Preferred MNQ resins are available commercially from Dow Corning and include MQ resin CF-0410.

The MQ resin is present at from 0.1 to 5% wt. of the composition and preferably at from 2 to 4% wt.

Preferably, the composition also comprises an oil selected from mineral oil, vegetable oil and animal oil. Preferably, such oil is present at from 1 to 30% wt. of the composition and more preferably from 3 to 10% wt.

EXAMPLE

Formulation

| Ingredient | % Wt. | | | | | | | |
|---|---|---|---|---|---|---|---|---|
| | 1 | 2 | 3 | 4 | 5 | A | B | C |
| EL-8050 | 75.14 | — | — | — | — | — | — | — |
| EL-8051 | — | — | — | — | 75.14 | — | — | — |
| EL-8052 | — | 65.79 | — | — | — | 40 | 20 | — |
| DC-9040 | — | — | 60.69 | — | — | — | — | — |
| DC-9041 | — | — | — | 72.81 | — | — | — | — |
| Caprylic/Capric Triglyceride(1) | 9.12 | 9.12 | 9.12 | 10.03 | 9.12 | 9.12 | 9.12 | 9.12 |
| Dicaprylyl Ether(2) | 13.69 | 13.69 | 13.69 | 15.06 | 13.69 | 13.69 | 13.69 | 13.69 |
| Trimethylated silica gel(3) | 0.05 | 0.4 | 0.1 | 0.1 | 0.05 | 2 | 3.2 | 1 |
| Decamethyl cyclopenta-siloxane(4) | 1 | 3 | 5 | 1 | 1 | 3 | 3 | 1 |
| Silicone oil(5) | — | 15 | 5 | — | — | 31.94 | 49.99 | 68.37 |
| Light Mineral Oil(6) | — | — | 7 | — | — | — | — | — |
| Fragrance | 1 | 1 | 1 | 1 | 1 | 1 | 1 | 1 |

(1)Crodamol GTCC ex. Croda
(2)Cetiol OE ex. Cognis
(3)VM-2270 Aerogel Fine Particles ex. Dow Corning
(4)MQ Resin CF-0410 ex. Dow Corning
(5)DC245 ex. Dow Corning
(6)Lytol ex. Sonnebourne Process
1. Weigh the full amount of elastomer into the vessel.
2. Start to mix at a slow speed (50-100 rpm) and gradually add the MQ Resin CF-0410.
3. Once the mixture is thoroughly blended add the fragrance.
4. In a side vessel weigh out the full amount of Lytol mineral oil and start the stirrer at a very low speed (50 rpm) ensuring the blades are under the liquid level to avoid aeration.
5. Gradually add the aerogel powder to the lytol whilst continually mixing. Add over a minimum of 10 minutes to ensure a smooth mix is achieved. Check there are no lumps in the mixture. This will form a thick liquid.
6. Add the crodamol to the lytol and aerogel premix and stir slowly until the air bubbles are fully released.
7. Slowly add the aerogel side mix to the main vessel containing the elastomer. Mix thoroughly but slowly to avoid aerating the batch.
8. Continue to mix until you have a smooth consistency and a translucent light product.

The invention claimed is:

1. A composition comprising from 40 to 95% wt. of the composition silicone elastomer 0.01 to 5% silica, and from 0 to 2% wt, water, wherein:
   the silica is pre-suspended in mineral oil or fragrance oil, and
   the composition is in the form of a hair treatment composition, and
   the silicone elastomer comprises dimethicone, vinyl dimethicone, hydrogendimethicone, and 2,4,6,8-tetravinyl cyclotetrasiloxane.

2. The composition according to claim 1 wherein the silica is fumed silica.

3. The composition according to claim 1 wherein the oil is light mineral oil.

4. The composition according to claim 1 wherein the oil is fragrance oil.

5. The composition according to claim 1 further comprising from 1 to 30% wt. volatile silicone.

6. The composition according to claim 1 wherein the composition further comprises a silicone elastomer comprising isododecane and dimethicone/bis-isobutyl PPG-20 crosspolymer.

7. The composition according to claim 1 wherein the composition further comprises a silicone elastomer comprising isodecyl neopentanoate and dimethicone/bis-lsobutyl PPG-20 crosspolymer.

8. The composition according to claim 1 wherein the composition further comprises a silicone elastomer comprising isohexadecane and dimethicone/bis-isobutyl PPG 20 crosspolymer.

9. The composition according to claim 1 wherein the composition further comprises a silicone elastomer comprising cyclopentasiloxane and dimethicone crosspolymer.

10. A composition comprising from 40 to 95% wt of the composition silicone elastomer, 0.01 to 5% silica, from 0 to 2% wt. water, and an MQ resin that is a condensation product between monofunctional silane (M) and tetrafunctional silane (Q), wherein the silicone elastomer comprises dimethicone, vinyl dimethicone, hydrogendimethicone, and 2,4,6,8-tetravinyl cyclotetrasiloxane.

11. The composition according to claim 10 wherein the MQ resin is present in an amount of from 0.1 to 5 wt % of the composition.

* * * * *